US012090106B2

(12) United States Patent
Weidner et al.

(10) Patent No.: US 12,090,106 B2
(45) Date of Patent: Sep. 17, 2024

(54) SYSTEM AND METHOD FOR THE REDUCTION OF FORCES ACTING ON AN ARM OF A HUMAN

(71) Applicant: EXOIQ GMBH, Hamburg (DE)

(72) Inventors: Robert Weidner, Gerdau (DE); Bernward Otten, Hamburg (DE)

(73) Assignee: EXOIQ GMBH, Hamburg (DE)

( * ) Notice: Subject to any disclaimer, the term of this patent is extended or adjusted under 35 U.S.C. 154(b) by 821 days.

(21) Appl. No.: 17/269,703

(22) PCT Filed: Aug. 17, 2019

(86) PCT No.: PCT/EP2019/072069
§ 371 (c)(1),
(2) Date: Feb. 19, 2021

(87) PCT Pub. No.: WO2020/038850
PCT Pub. Date: Feb. 27, 2020

(65) Prior Publication Data
US 2021/0315762 A1    Oct. 14, 2021

(30) Foreign Application Priority Data

Aug. 22, 2018  (DE) ...................... 10 2018 120 453.1

(51) Int. Cl.
*A61H 1/02*    (2006.01)
(52) U.S. Cl.
CPC ... *A61H 1/0281* (2013.01); *A61H 2201/1616* (2013.01); *A61H 2201/1626* (2013.01);
(Continued)
(58) Field of Classification Search
CPC .......... A61H 1/0281; A61H 2201/1616; A61H 2201/1614; A61H 2201/165; B25J 9/0048;
(Continued)

(56) References Cited

U.S. PATENT DOCUMENTS

| 4,180,870 A * | 1/1980 | Radulovic ............... A61F 5/013 601/33 |
| 2011/0164949 A1* | 7/2011 | Kim ...................... B25J 9/0006 414/1 |

(Continued)

FOREIGN PATENT DOCUMENTS

| DE | 26 15 209 A1 | 4/1976 |
| DE | 10 2016 104 879 A1 | 9/2017 |

(Continued)

OTHER PUBLICATIONS

International Search Report dated Oct. 15, 2019, issued in PCT Application No. PCT/EP2019/072069, filed Aug. 17, 2019.

(Continued)

*Primary Examiner* — Colin W Stuart
*Assistant Examiner* — Douglas Y Sul
(74) *Attorney, Agent, or Firm* — Workman Nydegger (57) ABSTRACT

A system having an arrangement for supporting an arm of a user is disclosed. The arrangement has an actuator, which is connected to a shoulder element by a joint chain. The joint chain is designed to extend along the shoulder blade of a shoulder of the user and to introduce vertically acting forces into the shoulder element. Moreover, the joint chain is guided by a flexible structure that extends over the shoulder of the user. By virtue of the deformability of the flexible structure, it is possible to ensure that a lifting of the shoulder, resulting from a lifting of a hand of the user, is not impeded.

15 Claims, 8 Drawing Sheets

(52) U.S. Cl.
CPC ............ *A61H 2201/1628* (2013.01); *A61H 2201/1638* (2013.01); *A61H 2201/165* (2013.01); *A61H 2201/1671* (2013.01); *A61H 2201/1676* (2013.01)

(58) Field of Classification Search
CPC ......... B25J 9/0006; F16C 11/00; F16C 11/04; F16C 11/045; F16C 11/12
See application file for complete search history.

(56) References Cited

U.S. PATENT DOCUMENTS

| | | | |
|---|---|---|---|
| 2016/0339583 A1* | 11/2016 | Van Engelhoven | ... B25J 9/0006 |
| 2017/0189257 A1* | 7/2017 | Lan | ... A63B 21/4017 |
| 2018/0303699 A1* | 10/2018 | Romo | ... A61F 5/013 |
| 2018/0361565 A1* | 12/2018 | Angold | ... B25J 9/106 |
| 2019/0240102 A1* | 8/2019 | Genani | ... A61H 1/0281 |
| 2019/0314978 A1* | 10/2019 | Hunt | ... B25J 9/0006 |
| 2020/0038219 A1 | 2/2020 | Mizera et al. | |
| 2020/0093676 A1 | 3/2020 | Mizera | |

FOREIGN PATENT DOCUMENTS

| | | |
|---|---|---|
| DE | 10 2016 121 203 A1 | 5/2018 |
| EP | 1 609 451 A1 | 12/2005 |
| EP | 3 156 193 A1 | 4/2017 |
| JP | 2017-024086 A | 2/2017 |
| KR | 2016-0104954 A | 9/2016 |
| WO | 2013/186705 A2 | 12/2013 |
| WO | 2018/065459 A2 | 4/2018 |
| WO | 2018/073629 A1 | 4/2018 |
| WO | 2018/224175 A1 | 12/2018 |

OTHER PUBLICATIONS

Written Opinion dated Oct. 15, 2019, issued in PCT Application No. PCT/EP2019/072069, filed Aug. 17, 2019.

* cited by examiner

SYSTEM AND METHOD FOR THE REDUCTION OF FORCES ACTING ON AN ARM OF A HUMAN

TECHNICAL FIELD

The present invention relates to exoskeletons. In particular, the present invention relates to exoskeletons adapted to support the arms.

BACKGROUND

Exoskeletons are typically adapted to natural movement patterns. To this end, the shoulder joint is of central importance. The main function of the shoulder joint is in the rotation of the upper arm bone (humerus) in the shoulder roof (acromion). The rotation allows for a total of three degrees of freedom. In addition, the shoulder blade is articulated to the breastbone (sternum) via the collarbone (clavicle) and gives the shoulder girdle two more degrees of freedom (up/down movement and back and forth movement of the shoulder girdle). The high complexity of the shoulder girdle makes it difficult to replicate the resulting movement patterns with little technical effort.

One approach to replication is based on hinge designs in which two elements are serially coupled about a vertical axis. The first element can, for example, be coupled to a support structure (e.g., a rucksack) and the second end can move freely in a plane parallel to the ground (cf., for example, document EP 3189945 A1). Different actuators that generate a torque about a horizontal axis can be attached to the free end. At the actuated end of the horizontal axis, a fastening option and/or a support surface for the upper arm can be arranged. The support structure and the connecting elements are typically designed in such a way that the actuated horizontal axis is aligned, as far as possible, to the pivot point of the humerus and the shoulder roof.

Another approach, which is shown for example in US 2012/184880 A1, is based on positioning a swivel joint over the shoulder, the swivel joint having a vertical axis of rotation which runs approximately through the shoulder joint (glenohumeral joint). A connecting element extends from the swivel joint to an actuated horizontal axis. In contrast to the approach described above, no tight connection to the arm of the user is required here, since the actuated axis cannot move freely in a plane parallel to the ground, but only around the vertical axis.

BRIEF DESCRIPTION OF THE INVENTION

According to the invention, forces which act on the arm in the vertical direction are (essentially) transmitted onto the support structure via a multi-link chain. In contrast to the approach described above, the remaining forces are not diverted via the arm of the user. Rather, the movement of the link chain is restricted (or guided) by a second, flexible structure which extends over the shoulder. This flexible structure can, for example, consist of two elements which (analogous to the second approach described above) are connected to one another by means of a joint that is arranged over the shoulder. Due to the deformability of the flexible structure, the system design is more compact, because the flexible structure can be arranged directly over the shoulder without obstructing raising the shoulder when the user raises his/her hand.

A system for reducing forces acting on an arm of a user according to the invention comprises a pelvic element for establishing a connection to the pelvis of the user, a shoulder element for establishing a connection to the user's shoulder girdle, a spinal element which connects the shoulder element to the pelvic element and which transmits forces acting on the shoulder element onto the pelvic element, and an arrangement for supporting the arm of the user. The arrangement comprises an actuator which is connected to the shoulder element by a link chain which extends along the shoulder blade of a shoulder of the user. The link chain exerts forces acting in the vertical direction onto the shoulder element and is guided by of a flexible structure which extends over the shoulder of the user.

The term "pelvic element", as used throughout the description and the claims, particularly is to be understood as a (partially flexible, e.g. textile) structure that surrounds or encloses the user's pelvis while the system is in use. Furthermore, the term "shoulder element", as used throughout the description and the claims, particularly is to be understood as a (partially flexible, e.g. textile) structure that surrounds or encloses the user's shoulders while the system is in use. Moreover, the term "spinal element", as used in the description and the claims, particularly is to be understood as an active or passive connecting structure consisting of several rigid or flexible elements which allow force to be transmitted between the shoulder element and the pelvic element.

In addition, the formulation "which extends along the shoulder blade of a shoulder of the user", as used in the description and the claims, particularly is to be understood as a link chain that extends at the level of the shoulder blade (essentially horizontally) from the back to one side of the body. Furthermore, the phrase "which extends over the shoulder of the user", as used in the description and the claims, particularly is to be understood as a flexible structure that is arranged vertically over the shoulder joint (and, for example, rests on the shoulder).

Preferably, the link chain is configured to allow for a movement of the actuator in a horizontal plane and to prevent movement of the actuator in the vertical direction. For example, the joints of the link chain may have parallel (vertical) axes of rotation.

In this regard, it is noted that the terms "horizontal" and "vertical", as used in the description and the claims, relate to a scenario in which the user is standing upright.

The flexible structure preferably has elements that are hingedly connected to one another.

For example, the hingedly interconnected elements can be rotatable relative to one another about an axis of rotation. The elements can be connected to one another in such a way that the axis of rotation extends in the vertical direction. In particular, the flexible structure may be configured to guide the actuator on a circular path lying in a horizontal plane. The pivot point of the shoulder joint is preferably in the center of the circular path.

Preferably, one of the hingedly connected elements has a curved section which is configured to allow for a vertical displacement of a part of the flexible structure by a vertical offset between the ends of the curved section. For example, the curved section may be L-shaped or U-shaped.

The system can be used in a method of reducing forces acting on an arm of a user, which comprises attaching the system to the pelvis and shoulder girdle of the user and controlling the actuator to reduce the forces acting on the arm of the person, wherein an obstruction to raising the shoulder, resulting from raising a hand of the user, is avoided by the deformability of the flexible structure.

Furthermore, all the features (of preferred embodiments) of the system according to the invention can also be features (of preferred embodiments) of the method according to the invention which relates to a (possible) use of the system according to the invention.

BRIEF DESCRIPTION OF THE DRAWINGS

In the following, the invention will be explained in more detail in the detailed description on the basis of exemplary embodiments, wherein reference is made to the drawings in which.

Notably, the shown elements are not necessarily depicted true to scale and in detail, but primarily serve to illustrate the inventive idea.

DESCRIPTION OF THE EMBODIMENTS

Figure 1:
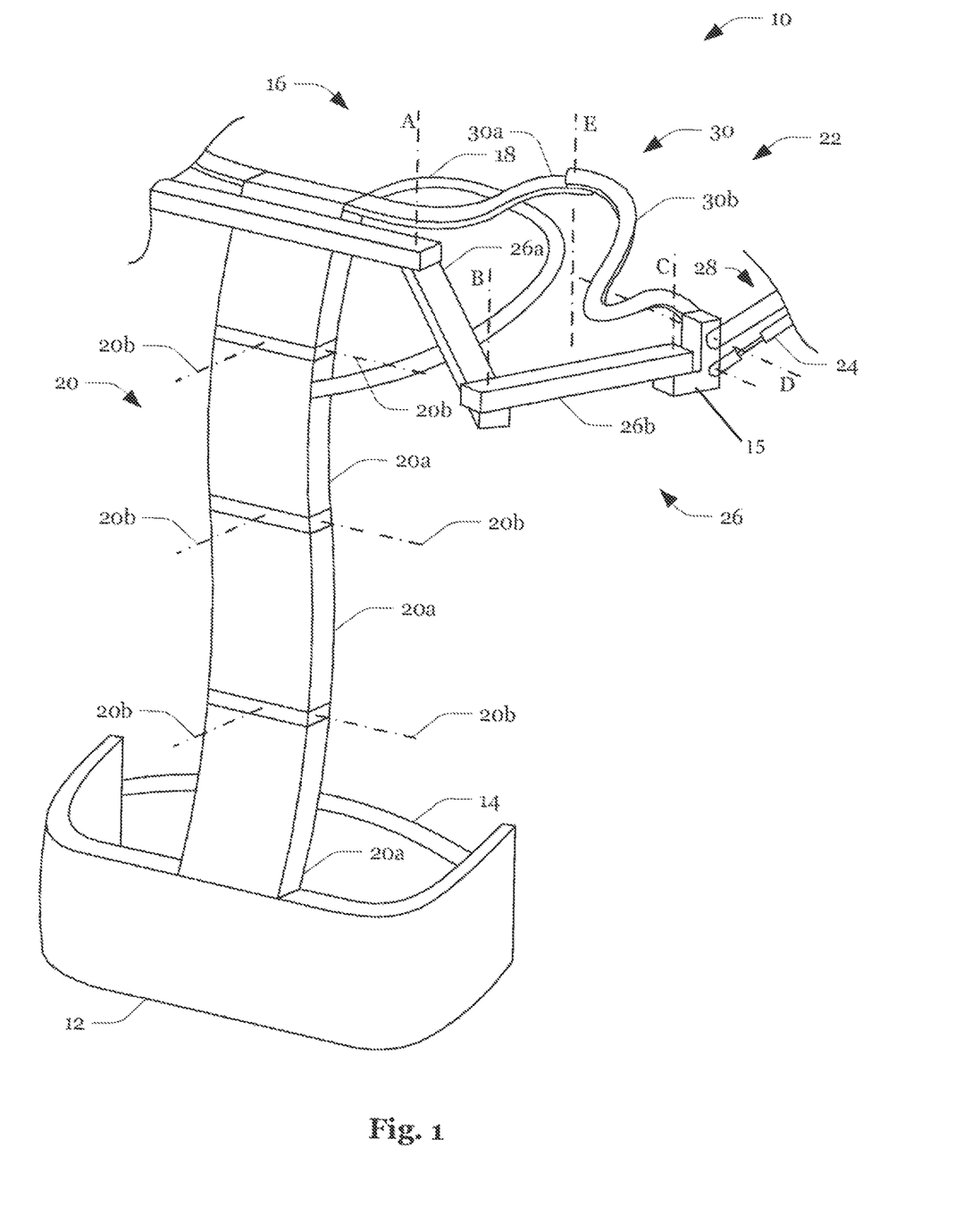
FIG. 1 is a schematic perspective view of a first system according to the invention.

FIG. 1 shows a system 10 for reducing forces acting on an arm of a user. The system 10 comprises a pelvis element 12 for establishing a connection to the pelvis of the user. When the system 10 is put on, the pelvic element 12 is arranged in such a way that it surrounds the user's pelvis and rests on the user's body, thereby enabling a transmission of force between the system 10 and the torso of the user. The pelvic element 12 can also be provided with a pelvic belt 14, or be integrated into a (textile) piece of clothing which encloses the pelvis of the user, to secure the force transmission.

The system 10 further comprises a shoulder element 16 for establishing a connection to the shoulder girdle of the user. When the system 10 is put on, the pelvic element 16 is arranged in such a way that it surrounds the user's pelvis and rests on the user's body, thereby enabling a transmission of force between the system 10 and the torso of the user. The shoulder element 16 may also be provided with shoulder straps 18 (only exemplary shown for the right shoulder in FIG. 1) or be integrated into a (textile) item of clothing which (partially or completely) encloses the shoulders of the user, to secure the force transmission.

The shoulder element 16 is connected to the pelvic element 12 by a spinal element 20 which transmits the forces acting on the shoulder element 16 onto the pelvic element 12. The spinal element 20 consists of a plurality of rigid segments 20a which are rotatable relative to one another about two (in the upright state, essentially) horizontal axes of rotation 20b, which allows bending the upper body. To support straightening the upper body, the spinal element 20 can be provided with one or more actuators (not shown) by means of which the relative positions of the segments 20a can be controlled.

Notably, the embodiment of the spinal element 20 shown in FIG. 1 is only an exemplary possibility and the invention is not limited in this regard. For example, instead of the rigid segments 20a, flexible segments 20a may be used, the rigidity of which is adjusted by means of actuators, and the relative rotation of the segments 20a may be superimposed with a relative displacement of the segments 20a. In addition, the spinal element 20 may comprise more or fewer segments 20a than shown in FIG. 1.

As shown in FIG. 1, an arrangement 22 for supporting the arm of the user is coupled to the shoulder element 16. The arrangement 22 has an actuator 24 in the form of a pneumatic cylinder which is connected to the shoulder element 16 by a two-link link chain 26 and a connector member 15. The link chain 26 comprises a first element 26a, wherein a first end of the first element 26a is rotatably coupled to the shoulder element 16 about a vertical axis A, and a second element 26b, wherein a first end of the second element 26b is rotatably coupled to the second end of the first element 26a about a vertical axis B. As shown in FIG. 1, the actuator 24 is rotatably coupled to connector member 15 which is rotatably coupled to the second end of the second element 26b about a vertical axis C and causes a rotary movement of an upper arm, forearm, or wrist support 26 about a horizontal axis D.

The link chain 26 is also guided by means of a flexible structure 30 which spans the user's shoulder (or rests on the user's shoulder). The flexible structure 30 is pliable in the vertical direction and thus transmits (almost) no forces in the vertical direction. As shown in FIG. 1, the flexible structure 30 may comprise two elements 30a, 30b which are articulated to one another (rotatable about an axis of rotation E extending in the vertical direction). One end of flexible structure 30 is coupled directly to connector member 15. If the arm support 26 is designed as an upper arm support and the axes of rotation D and E intersect at the pivot point of the shoulder joint, the upper arm can be supported in its natural movement pattern.

In order to obstruct raising the shoulder, resulting from raising a hand of the user, as little as possible, one of the articulated elements 30a, 30b has a curved, U-shaped section which is provided for vertical displacement of a part of the flexible structure 30 by a vertical offset between the ends of the curved section. In other words, the second element 30b of the flexible structure 30 is guided between the actuator 24 and the pivot point over the shoulder in the form of two "L" on a non-direct path. This facilitates raising the shoulder, but also allows the actuator 24 to be guided reliably in a circular path around the shoulder pivot point. A similar indirect force flow can also be provided for the first element 30a of the flexible structure 30.

Figure 2:
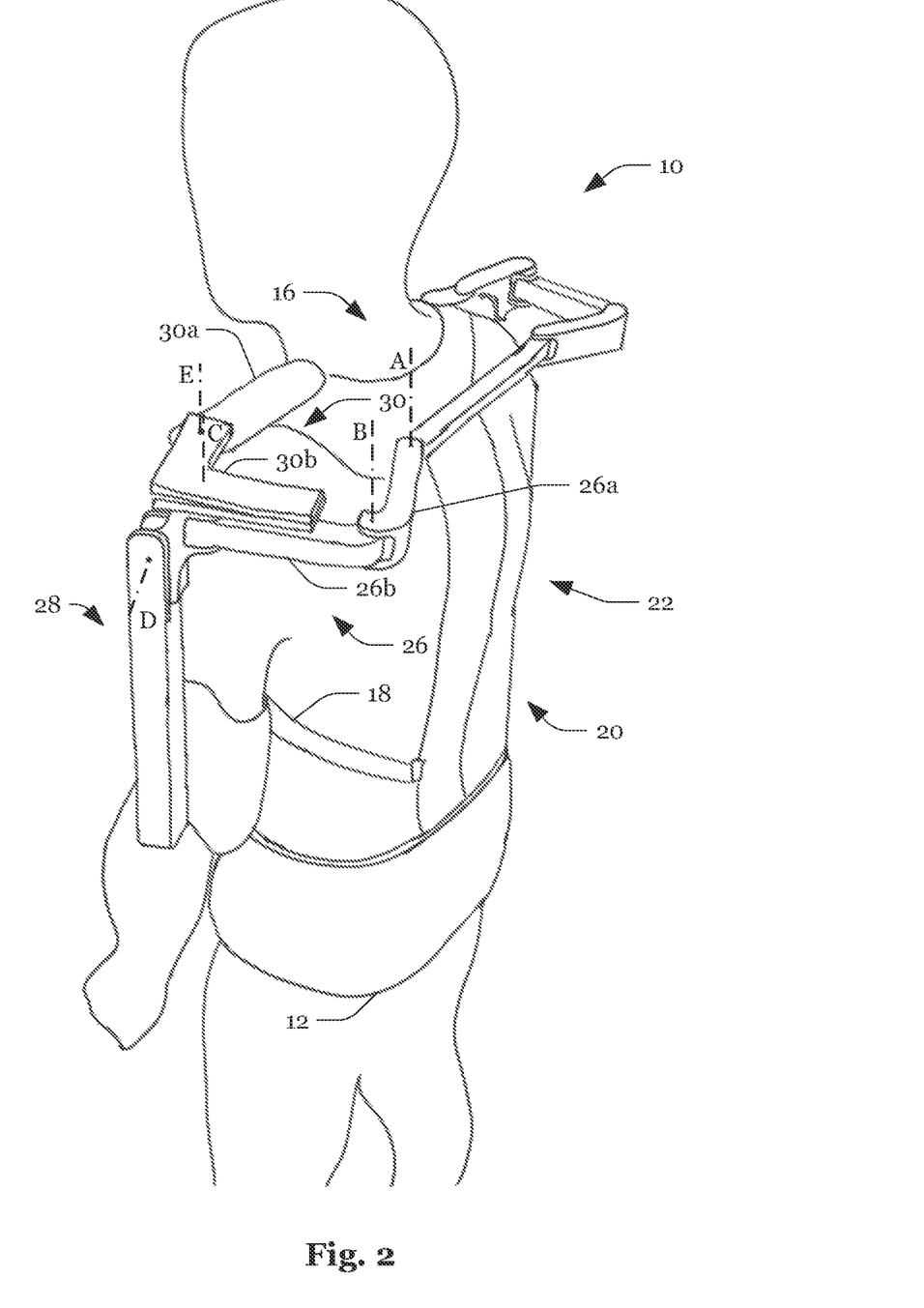
FIGS. 2 to 4 are schematic perspective views of a second system according to the invention.
Figure 3:
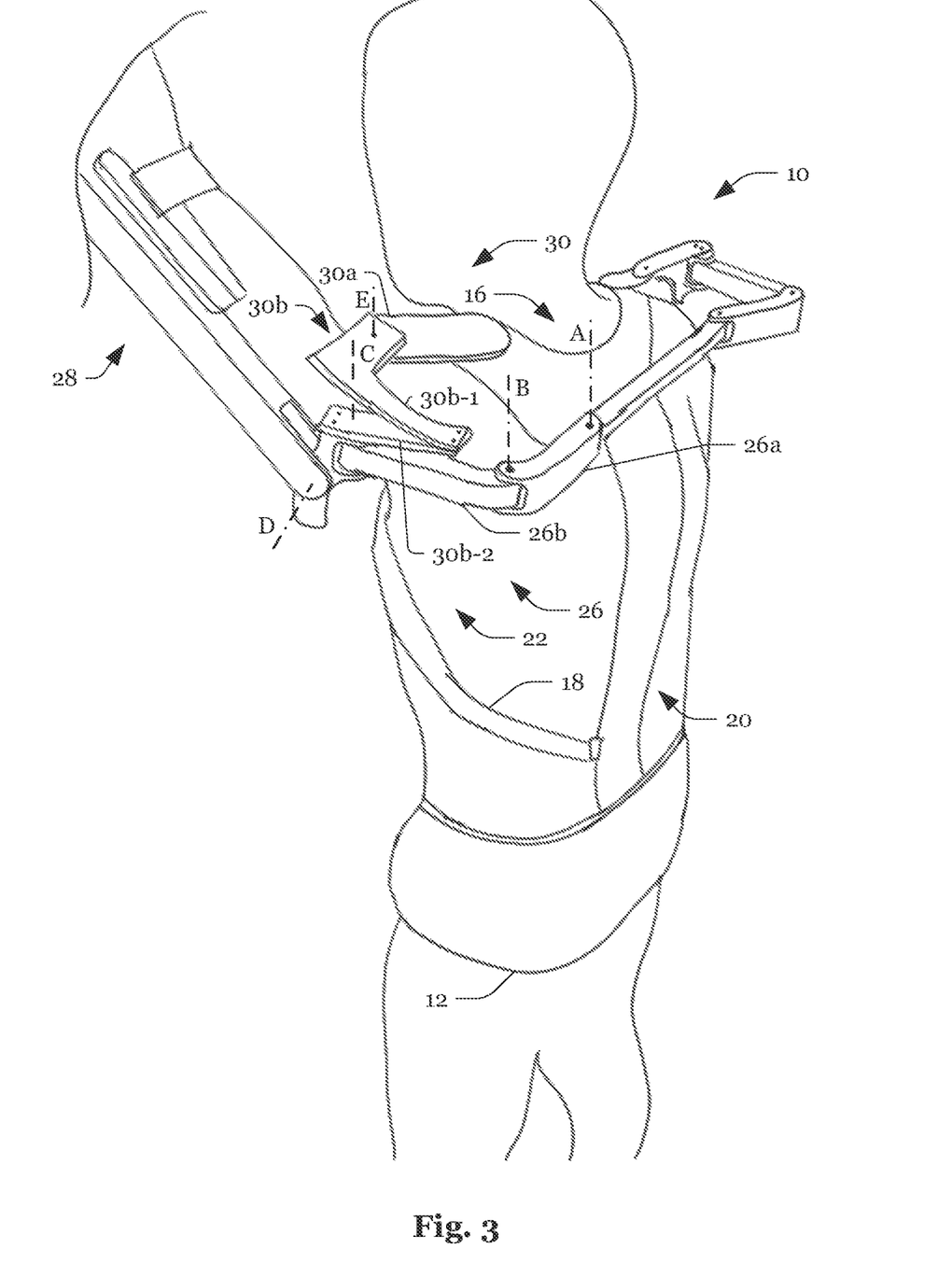
Figure 4:
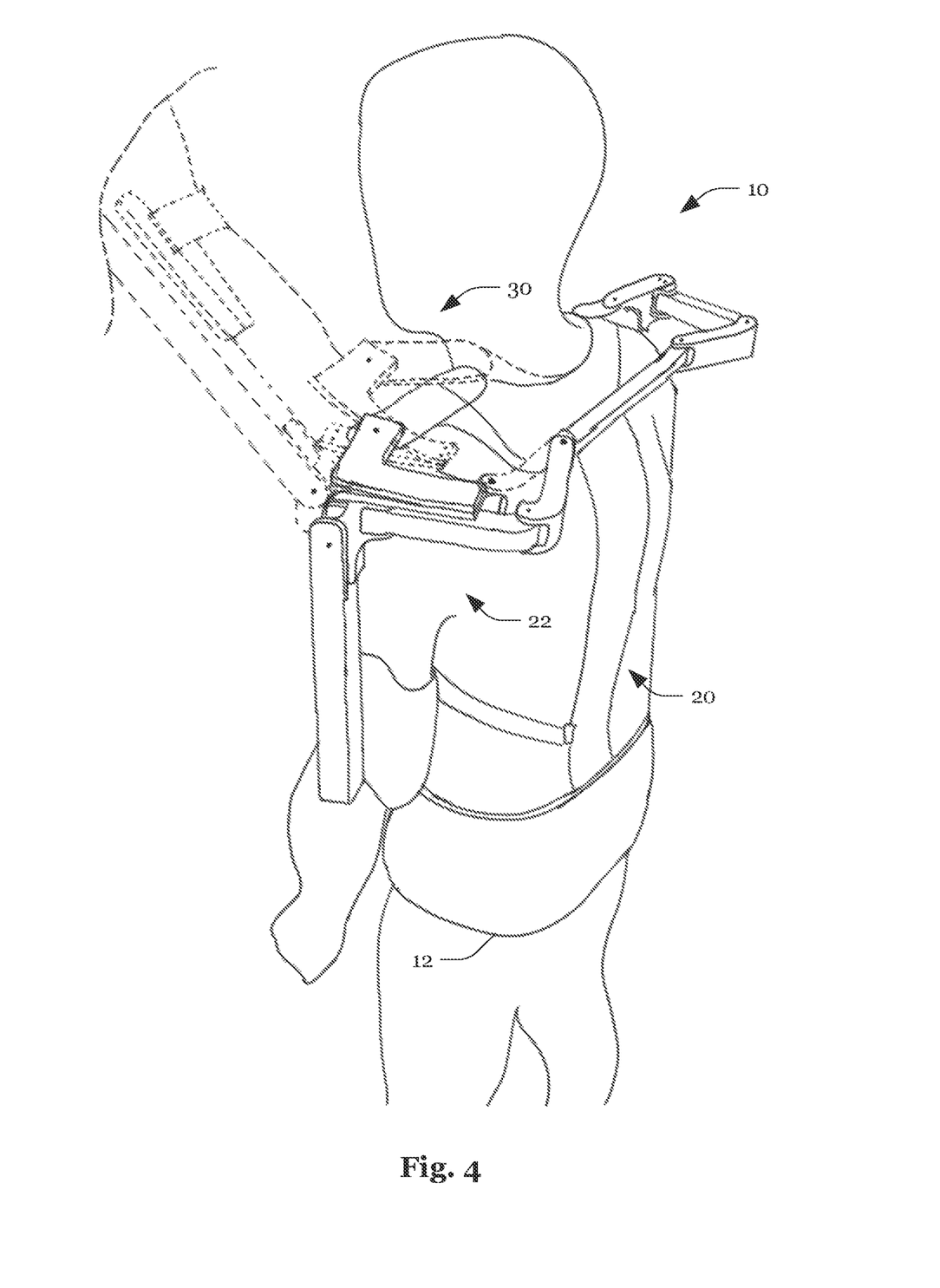

FIG. 2 shows a further possible embodiment of a system 10 according to the invention, which differs from the system 10 shown in FIG. 1 in that the second element 30b of the flexible structure has an L-shaped section 30b-1, the distal end of which is connected to the link chain 26 by a connecting element 30b-2. As shown in FIG. 3, the material of the second element 30b is chosen such that when the shoulder is raised, the initially flat L-shaped section 30b-1 can be bent away from the initially flat connecting piece 30b-2 in the vertical direction (whereby the L-shaped section is twisted). As illustrated in FIG. 4, the flexible structure 30 gives way when the arm is raised, so that no gap must be provided between the flexible structure 30 and the shoulder (when the arm is lowered) and the system 10 can be designed to be more compact.

Figure 5:
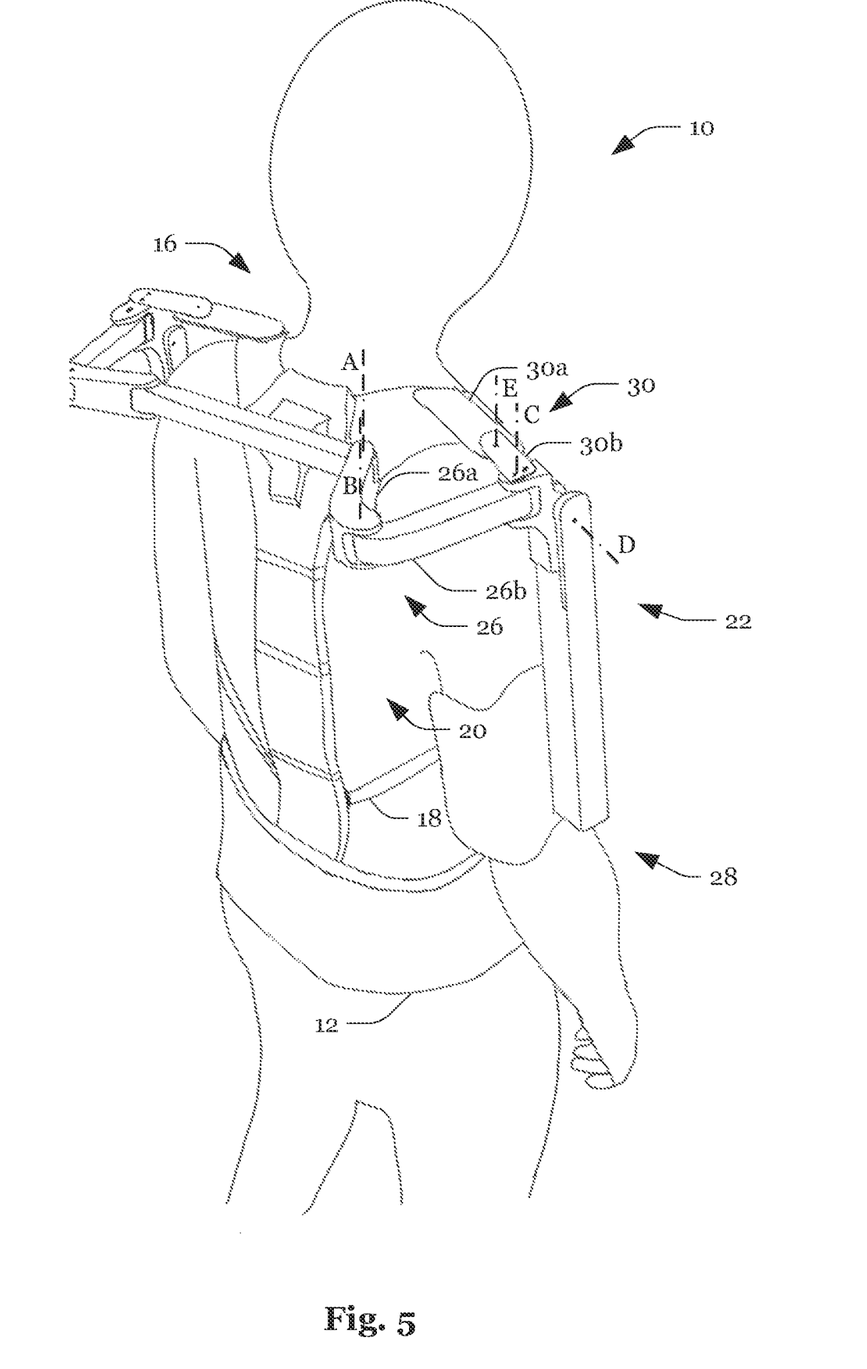
FIGS. 5 to 7 are schematic perspective views of a third system according to the invention.
Figure 6:
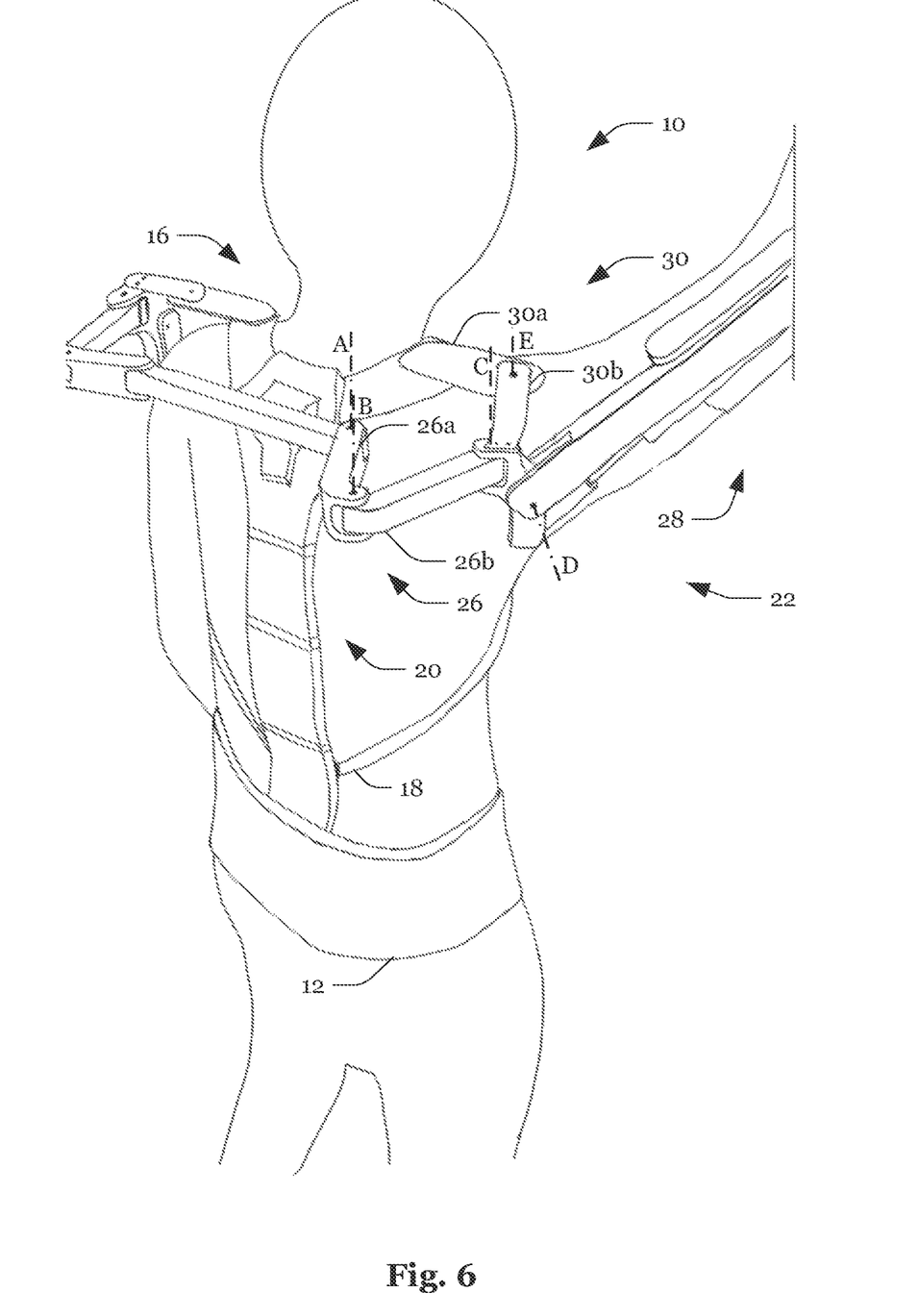
Figure 7:
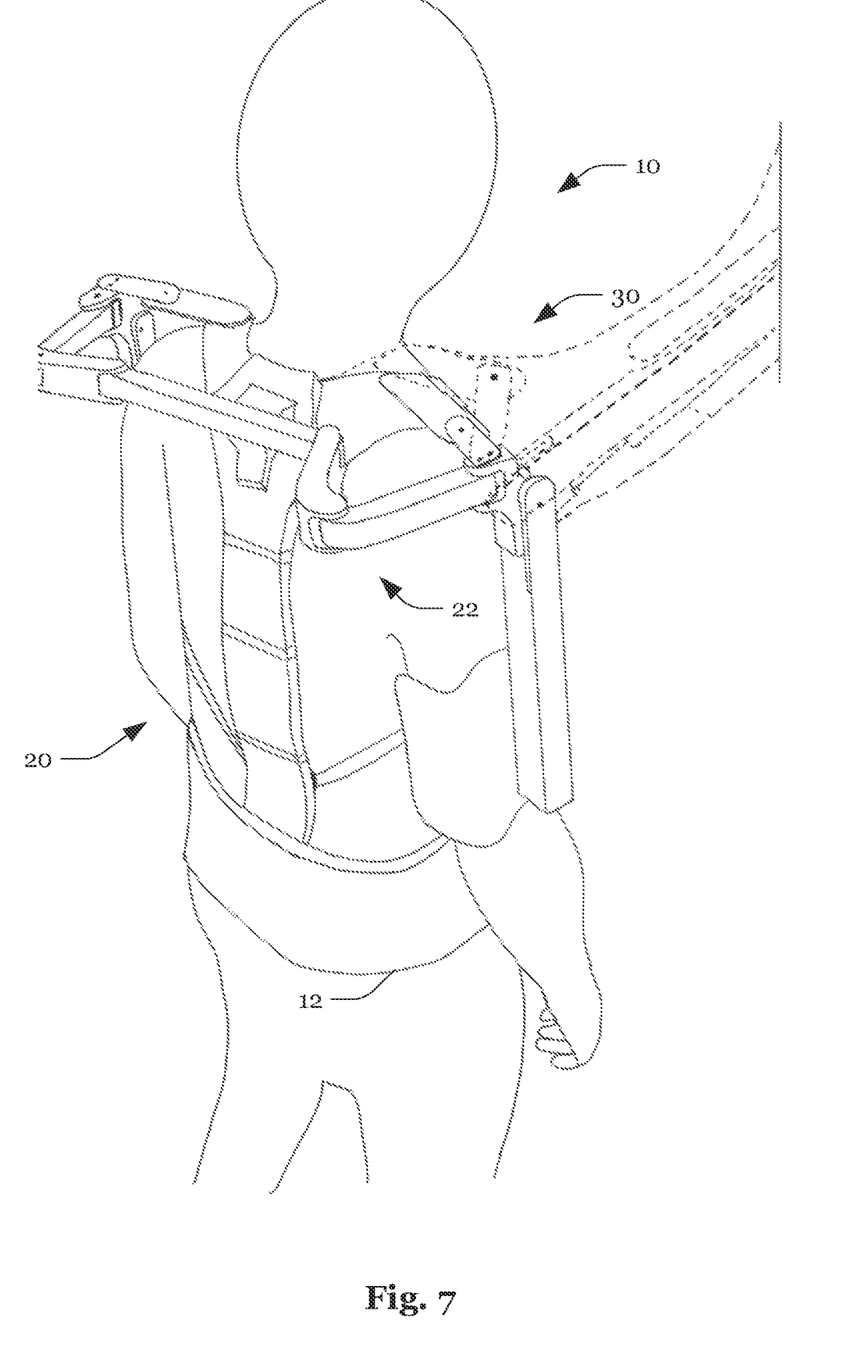

FIGS. 5 to 7 show a further possible embodiment of a system 10 according to the invention, which differs from the system 10 shown in FIGS. 2 to 4 in that the second element 30b is designed as a flexible (textile) band. As shown in FIG. 6, the material of the flexible band is selected such that it expands when the shoulder is raised and thus compensates for the resulting increased height offset. As illustrated in FIG. 7, the raising of the user's shoulder is thus not hindered when the arm is raised, since the flexible band stretches over the shoulder, but does not block the shoulder movement.

Figure 8:
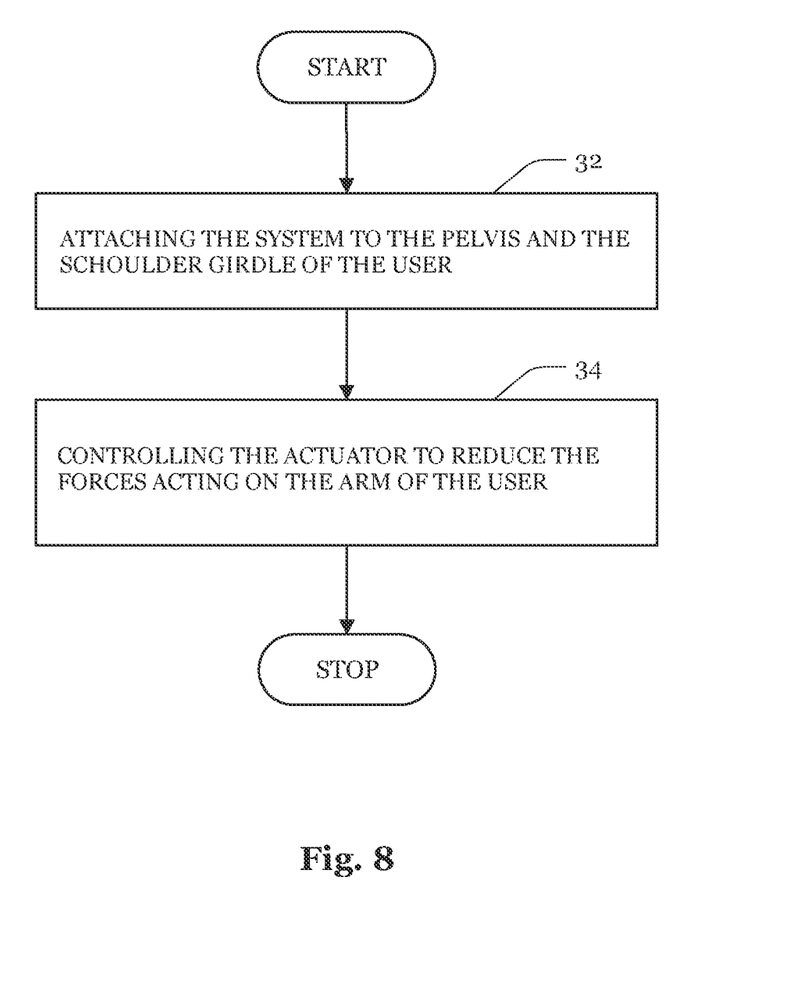
FIG. 8 shows a flow chart of a method of reducing forces acting on an arm of a user.

FIG. 8 shows a method of reducing the forces acting on an arm of a user. In step 32, the pelvis element 12 is connected to the pelvis and the shoulder element 16 is connected to the shoulders, and in step 34, the actuator 24 is controlled to reduce the forces acting on the arm of the person. For example, the system 10 can be provided with sensors, from the measured values of which a load condition of the user can be derived and the user can be supported according to his load condition. In particular, the user can be supported in an activity in which the user holds his hands above his head in order to prevent fatigue of the user or to reduce a strain that the user otherwise could not cope with.

LIST OF REFERENCE SIGNS 10 system
12 pelvic element
14 pelvic belt
16 shoulder element
18 shoulder strap
20 spinal element
20a segment
20b axis of rotation
22 arrangement
24 actuator
26 link chain
26a element (link chain)
26a element (link chain)
28 (arm) support
30 flexible structure
30a element
30b element
30b-1 L-shaped section
30b-2 connector
32 process step
34 process step
A-E rotary axes

The invention claimed is:

1. A system for reducing forces acting on an arm of a user, comprising:
a pelvic element which is configured to be connected to the user's pelvis;
a shoulder element which is configured to be connected to the user's shoulder girdle;
a spinal element which connects the shoulder element and the pelvic element and is configured to transmit forces exerted on the shoulder element onto the pelvic element; and
an arrangement for supporting the arm of the user;
wherein the arrangement comprises a link chain being configured to extend along the shoulder blade of a shoulder of the user and to transmit forces acting in the vertical direction to the shoulder element, the link chain comprising at least a first link element hingedly coupled to a second link element, the link chain having a first end hingedly coupled to the shoulder element and an opposing second end hingedly coupled directly to a connector member, the arrangement further comprising an actuator coupled to the connector member;
wherein the link chain is guided by a flexible guide structure which is configured to extend over the shoulder of the user, the flexible guide structure comprising an elongated first guide element having a first end directly coupled to the connector member and an opposing second end, the elongated first guide element being flexible between the first end and the opposing second thereof so that the first guide element can bend during use;
wherein the link chain is configured to allow a movement of the actuator in a horizontal plane and prevent movement of the actuator in the vertical direction, when the user stands upright.

2. The system of claim 1, wherein the joints of the link chain have parallel axes of rotation.

3. The system of claim 2, wherein the parallel axes of rotation is configured to extend in the vertical direction when the user stands upright.

4. The system of claim 1, wherein the link chain is a planar swivel link chain.

5. The system of claim 1, wherein the flexible guide structure comprises one or more elongated and/or flat elements, which are configured to exert a guiding force against a pulling direction onto the link chain.

6. The system of claim 5, wherein the one or more elongated and/or flat elements are bendable or pliable transversely to the direction of pull.

7. The system of claim 1, wherein the flexible guide structure has elements which are hingedly connected to one another.

8. The system of claim 7, wherein an axis of rotation of the elements which are hingedly connected to one another is configured to extends in the vertical direction, when the user stands upright.

9. The system of claim 8, wherein the flexible guide structure is configured to guide the actuator on a circular path lying in a horizontal plane, when the user-is stands upright.

10. The system of claim 9, wherein the flexible guide structure is configured so that the pivot of the shoulder joint of the user is in the center of the circular path during use.

11. The system of claim 7, wherein one of the hingedly connected elements has a curved section which is configured to allow for a vertical displacement of a part of the flexible guide structure by a vertical offset between the ends of the curved section.

12. The system of claim 11, wherein the curved section is L- or U-shaped.

13. A method of reducing forces acting on an arm of a user, comprising:
attaching the system of claim 1 to the pelvis and the shoulder girdle of the user; and
controlling the actuator to reduce the forces acting on the arm of the user;
wherein an obstruction to raising the shoulder, resulting from raising a hand of the user, is avoided by the deformability of the flexible guide structure.

14. The system of claim 1, wherein the actuator is directly hingedly coupled to the connector member.

15. An exoskeleton system for reducing forces acting on an arm of a user, comprising:
a pelvic element comprising a pelvic belt;
a shoulder element;
an elongated spinal element having a first end connected to the pelvic element and an opposing second end connected to the shoulder element;
an arm support arrangement comprising:
a link chain that is movable relative to the shoulder element, the link chain comprising a first link element hingedly coupled to a second link element, the first link element having a first end hingedly coupled to a connector member and an opposing second end hingedly coupled to a first end of the second link element, the second link element having a second end hingedly coupled to the shoulder element;

an actuator coupled to the connector member; and a guide structure that guides the movement of the link chain, the guide structure comprising a first guide element hingedly coupled to a second guide element, the first guide element having a first end directly coupled to the connector member and an opposing second end hingedly coupled to a first end of the second guide element, the second guide element having a second end coupled to the shoulder element or the spinal element, the first guide element being flexible between the first end and the opposing second thereof so that the first guide element can bend during use;

wherein the link chain is configured to allow a movement of the actuator in a horizontal plane and prevent movement of the actuator in the vertical direction, when the user stands upright.

* * * * *